United States Patent
Gozani et al.

(10) Patent No.: US 7,917,201 B2
(45) Date of Patent: Mar. 29, 2011

(54) METHOD AND APPARATUS FOR DETERMINING OPTIMAL NEUROMUSCULAR DETECTION SITES, NOVEL DIAGNOSTIC BIOSENSOR ARRAY FORMED IN ACCORDANCE WITH THE SAME, AND NOVEL METHOD FOR TESTING A PATIENT USING THE NOVEL DIAGNOSTIC BIOSENSOR ARRAY

(75) Inventors: Shai N. Gozani, Brookline, MA (US); Marie Neverov, Stoneham, MA (US); Charles Fendrock, Sudbury, MA (US); Michael Williams, Melrose, MA (US)

(73) Assignee: NeuroMetrix, Inc., Waltham, MA (US)

( * ) Notice: Subject to any disclaimer, the term of this patent is extended or adjusted under 35 U.S.C. 154(b) by 170 days.

(21) Appl. No.: 11/508,364

(22) Filed: Aug. 23, 2006

(65) Prior Publication Data

US 2008/0077041 A1    Mar. 27, 2008

(51) Int. Cl.
*A61B 5/05* (2006.01)
*A61B 5/04* (2006.01)
*A61B 5/103* (2006.01)
*A61B 5/117* (2006.01)

(52) U.S. Cl. ........ 600/547; 600/372; 600/382; 600/384; 600/587

(58) Field of Classification Search .................. 600/300, 600/301, 306, 372, 382, 384, 386, 393, 544, 600/546, 547, 554, 587; 606/32, 34, 35, 606/41

See application file for complete search history.

(56) References Cited

U.S. PATENT DOCUMENTS

| | | |
|---|---|---|
| 5,560,372 A | 10/1996 | Cory |
| 5,775,331 A | 7/1998 | Raymond et al. |
| 5,976,094 A | 11/1999 | Gozani |
| 2002/0183605 A1 | 12/2002 | Devlin et al. |
| 2004/0225211 A1* | 11/2004 | Gozani et al. ............... 600/382 |
| 2005/0101876 A1 | 5/2005 | Pearlman |
| 2006/0015028 A1 | 1/2006 | Finneran et al. |

* cited by examiner

*Primary Examiner* — Jeffrey G Hoekstra
(74) *Attorney, Agent, or Firm* — Pandiscio & Pandiscio

(57) ABSTRACT

This invention relates to the detection of bioelectric signals indicative of neuromuscular function. A mapping biosensor array is first used to identify, relative to reliable anatomical landmarks, the optimal myoelectrical detection site for the majority of the population. Then a diagnostic biosensor array is fabricated using this information so that when the diagnostic biosensor array is positioned on an individual using the reliable anatomical landmarks, the detection electrode is automatically positioned over the optimal detection site.

11 Claims, 9 Drawing Sheets

Fixed geometry sensor with motor point detector electrode encompassing grid elements of optional CMAP response over motor point, and other parts of fixed geometry sensor.

Volume-conducted Compound Muscle Action Potential compared to an over-muscle Compound Muscle Action Potential in the same subject.

Left hand reference stimulation electrodes and detector electrode grid with fixed geometry.

Subject with grid map on muscle of interest.

Flowchart to determine the CMAP amplitude for each grid element for each subject.

Flowchart to map grid elements across sujects according to CMAP amplitude.

Flowchart to map grid elements across subjects according to frequency of maximum CMAP amplitude for each grid element.

B2P map, averaged over ten subjects

| [5-A] 0.9 | [5-B] 2.56 | [5-C] 0.74 | [5-D] 1.7 | [5-E] 1.97 |
|---|---|---|---|---|
| [4-A] 2.1 | [4-B] 2.84 | 4-C] 2.71 | [4-D] 2.73 | [4-E] 2.89 |
| [3-A] 3.65 | [3-B] 7.17 | [3-C] 8.68 | [3-D] 6.07 | [3-E] 2.63 |
| [2-A] 4.02 | [2-B] 8.41 | [2-C] 8.46 | [2-D] 5.64 | [2-E] 1.96 |
| [1-A] 2.08 | [1-B] 3.69 | [1-C] 3.15 | [1-D] 1.77 | [1-E] 1.54 |

CMAP Amplitude map in millivolts, averaged over ten subjects.

map of normalized B2P, averaged over ten subjects

| [5-A] 0.09 | [5-B] 0.25 | [5-C] 0.07 | [5-D] 0.16 | [5-E] 0.18 |
|---|---|---|---|---|
| [4-A] 0.2 | [4-B] 0.27 | 4-C] 0.26 | [4-D] 0.26 | [4-E] 0.28 |
| [3-A] 0.34 | [3-B] 0.68 | [3-C] 0.83 | [3-D] 0.58 | [3-E] 0.27 |
| [2-A] 0.38 | [2-B] 0.8 | [2-C] 0.81 | [2-D] 0.55 | [2-E] 0.2 |
| [1-A] 0.2 | [1-B] 0.36 | [1-C] 0.31 | [1-D] 0.17 | [1-E] 0.14 |

Normalized CMAP Amplitude, averaged over ten subjects

Fixed geometry sensor with motor point detector electrode encompassing grid elements of optional CMAP response over motor point, and other parts of fixed geometry sensor.

| CMAP Amplitude | Over-Muscle mV | Volume-Conducted, mV |
|---|---|---|
| Min | 4.29 | 0.44 |
| Max | 10.42 | 1.29 |
| Mean | 7.68 | 0.81 |

Over-Muscle CMAP amplitude at the Motor Point vs. Volume Conducted CMAP amplitude in milliVolts, averaged over 30 waveforms in the abductor pollicis brevis muscle in the left and right hands of 15 different individuals.

TABLE 1

METHOD AND APPARATUS FOR DETERMINING OPTIMAL NEUROMUSCULAR DETECTION SITES, NOVEL DIAGNOSTIC BIOSENSOR ARRAY FORMED IN ACCORDANCE WITH THE SAME, AND NOVEL METHOD FOR TESTING A PATIENT USING THE NOVEL DIAGNOSTIC BIOSENSOR ARRAY

FIELD OF THE INVENTION

This invention relates to methods and apparatus for the assessment of neuromuscular function. More particularly, this invention relates to methods and apparatus for the improved detection of signals indicative of neuromuscular function.

BACKGROUND OF THE INVENTION

There are many clinical and non-clinical situations which call for a rapid, reliable and low-cost assessment of neuromuscular function.

Neuromuscular dysfunction relates to pathologies of the peripheral nerves and muscles.

Neuromuscular Disorders

Neuromuscular disorders are relatively common and many are well known to the general public. By way of example, Carpal Tunnel Syndrome (CTS) is a common form of neuromuscular disease. CTS arises from compression of the median nerve in the region where the median nerve traverses the wrist. CTS typically causes discomfort and/or loss of sensation in the hand and, in severe cases, may compromise use of the hand. Highly repetitive wrist movements are believed to be one cause of CTS.

Other common medical conditions (e.g., diabetes, rheumatoid arthritis and cancer) are also associated with neuromuscular disease.

Peripheral nerves are comprised of motor and sensory nerves. Motor nerves control muscles and sensory nerves carry sensory information from the periphery into the central nervous system.

Motor nerve function is generally assessed by electrically stimulating a nerve and then measuring the bioelectrical response of the muscle innervated by that nerve. The muscle response is detected by measuring the myoelectric potential generated by the muscle in response to the stimulus applied to the nerve.

Sensory nerve function is generally assessed by electrically stimulating a sensory nerve, at a first point along the nerve, and then measuring the bioelectrical response of the same nerve at a second point along the nerve at a known distance from the stimulation site.

With respect to neuromuscular function, one indication of the physiological state of the nerve is provided by the time delay occurring between the application of the stimulus to the nerve and the detection of the resulting bioelectrical response, where the bioelectrical response may be in the muscle or in the nerve itself. In the case of neuromuscular disease affecting motor nerves, if the nerve is damaged, conduction of the signal via the nerve to the muscle, and hence detection of the muscle's resulting myoelectrical response, will be slower than in a healthy nerve. Correspondingly, in the case of disease affecting sensory nerves, if the nerve is damaged, conduction of the nerve from the stimulation site to the detection site will be slower than in a healthy nerve. Thus, an abnormally long delay between the application of a stimulus to the nerve and the detection of a muscle or sensory response generally indicates impaired neuromuscular function.

Automated Devices for Assessing Neuromuscular Function

Automated devices have recently been introduced into the marketplace to assess neuromuscular function in physician offices. These automated devices are designed to be used by clinical personnel without specialized neurophysiology training.

U.S. Pat. No. 5,976,094 to Gozani discloses one such device that is successfully used thousands of times a year to make diagnostic assessments of peripheral nerves. The Gozani device utilizes a diagnostic biosensor array comprising at least one proximal stimulation electrode that is set in a fixed geometric relationship to at least one distal detection electrode. The stimulation electrode applies an electrical stimulation to a nerve, and the detection electrode detects the bioelectric potential (i.e., signal) that is evoked downstream of the stimulation site, either in the muscle innervated by that nerve (in the case of the assessment of motor nerves) or in the nerve itself (in the case of the assessment of sensory nerves).

"Volume-Conducted" Signals

As noted above, in the case of motor nerves, the myoelectric potential is evoked in the muscle innervated by a nerve, and is detected by a detection electrode. In the case of sensory nerves, the bioelectrical potential is generated in the nerve downstream from the stimulation site, and is detected by a detection electrode. The bioelectrical signal must pass through the volume of body tissue which lies between (i) the source of the bioelectrical signal (i.e., in the case of motor nerves, the muscle that is innervated by the stimulated nerve, and in the case of sensory nerves, the nerve itself), and (ii) the detection electrode. The extent of this volume of tissue is generally a function of (i) the depth of the signal source (i.e., how deep the signal source lies relative to the surface-mounted detection electrode), and (ii) the lateral offset of the detection electrode (i.e., how far the detection electrode lies from a position directly overhead the source of the bioelectrical signal). Signal conduction through a volume of intervening tissue, where there is commonly a substantial lateral offset, is sometimes referred to as a "volume-conducted" signal.

With respect to neuromuscular function, volume-conducted signals are generally reliable for determining the time delay between the application of the proximal stimulus to the nerve and the detection of the distal response in the muscle. However, there is generally a substantial lateral offset and the myoelectric potential typically travels through several centimeters of body tissue before reaching the detection electrode. As a result, the volume-conducted signal is typically filtered to a substantial extent by the intervening tissue, which may result in small changes to the waveform shape, and, more critically, in a significant reduction in signal amplitude.

Sensory nerve responses generally cannot be effectively detected as volume-conducted signals, and typically must be measured directly over the source nerve.

There are certain advantages to recording myoelectrical responses using detection electrodes placed so as to measure the volume-conducted response. One such advantage is that the detection electrodes do not need to be placed in a precise location over the muscle, which may be challenging for clinical personnel lacking specialized neurophysiology training.

While automated devices using volume-conduction-based myoelectrical measurements for assessing neuromuscular function generally work well in a clinical setting, the aforementioned signal filtering associated with volume-conducted signals may place some limits on the clinical utility of the results. Thus, a waveform with sharper definition and more distinct features in the time domain, and with greater amplitude, would enable such automated devices to make even more precise assessments of neuromuscular function.

"Over-Muscle" Signals

When assessing neuromuscular function, it is also possible to use another approach which can sometimes provide a superior (i.e., sharper, more distinct and higher-amplitude) signal from the evoked myoelectric potential. More particularly, with this alternative approach, the nerve is stimulated in the manner described above, but the evoked myoelectric potential is detected directly over the nerve at the point where the nerve innervates the muscle, i.e., at the "motor point". Since the evoked signal is detected very close to the myoelectric potential source (i.e., directly over the motor point, with effectively no lateral offset), this alternative approach has the benefit of providing a signal which arrives at the detection electrode after passing through significantly less intervening tissue. As a result, the signal is subject to less filtering and hence has more distinct waveform features and characteristics in the time domain, and much greater amplitude. Thus, the relatively intact signal can be used to make a more accurate assessment of neuromuscular function. A signal detected at the motor point is sometimes referred to as an "over-muscle" signal.

A major drawback to detecting the myoelectrical signal directly over the motor point is that it is first necessary to find the precise location of the motor point. Unfortunately, this point cannot generally be located by visual inspection or palpation. More particularly, due to normal variations in the neuromuscular anatomies of the human body, and due to the fact that nerves and muscle are generally located below the surface of the skin without obvious anatomical indication, precise placement of the detection electrode over the motor point is a rather uncertain matter, even for an experienced medical practitioner.

In general clinical practice, in order to reliably locate a motor point, a trained neurologist must search for the target location by electrically examining multiple sites disposed across a significant range of the anatomy. More particularly, the target location is generally found by placing the detection electrode at a first location, applying a stimulus and detecting a response signal, then moving the detection electrode to a different location, applying another stimulus and detecting another response signal, and then repeating this process until the target motor point is located (i.e., at the point of the most-distinct and largest signal). This is a time-consuming process that requires a specially-trained individual.

It is, therefore, a primary object of the present invention to provide (i) a novel method and apparatus for determining an optimal neuromuscular detection site (e.g., for locating the motor point), (ii) a novel diagnostic biosensor array formed in accordance with the same, and (iii) a novel method for testing a patient using the novel diagnostic biosensor array, all for use in a physician's office by clinical personnel without specialized neurophysiology training.

SUMMARY OF THE INVENTION

In accordance with the present invention, there is provided (i) a novel method and apparatus for determining an optimal neuromuscular detection site (e.g., for locating the motor point), (ii) a novel diagnostic biosensor array formed in accordance with the same, and (iii) a novel method for testing a patient using the same, all for use in a physician's office by clinical personnel without specialized neurophysiology training.

In one preferred form of the present invention, a mapping biosensor array is provided for determining an optimal neuromuscular detection site, e.g., for locating the motor point. The mapping biosensor array preferably comprises a stimulation electrode and a detection electrode grid, wherein the detection electrode grid comprises a plurality of sensor cells.

And in one preferred form of the present invention, there is provided a mapping biosensor array for applying a stimulus to a test subject and for detecting the resulting signal at a plurality of detection sites, and means for comparing the same, whereby to determine an optimal neuromuscular detection site, e.g., the motor point.

And in one preferred form of the invention, there is provided a diagnostic biosensor array for applying a stimulus to a patient and for detecting a resulting signal at an optimal neuromuscular detection site, e.g., at the motor point.

Preferably the diagnostic biosensor array is constructed using information obtained by using the mapping biosensor array.

In accordance with the present invention, the mapping biosensor array and the diagnostic biosensor array are both positioned on the individual by referencing a known anatomical landmark, e.g., where the motor point of the median nerve is being targeted, the mapping biosensor array and the diagnostic biosensor array would both be positioned on the individual using the intersection of the palmaris longus tendon and the wrist crease as a reference point. Of course, the specific anatomical landmark used will depend on the particular anatomical structure being targeted, but in any case the anatomical landmark is selected so as to be familiar and easy for non-experts to locate, thus facilitating the correct placement of both the mapping biosensor array and the diagnostic biosensor array relative to the anatomy, and thereby enhancing the accuracy of the results.

As noted above, in order for the diagnostic biosensor array to acquire a signal with more distinct features and characteristics in the time domain, and with greater amplitude, than that of a volume-conducted signal, the detection electrode must be positioned substantially directly over the motor point. The aforementioned difficulty in the prior art of precisely locating the motor point is addressed, in the present invention, through the use of the novel mapping biosensor array. More particularly, the mapping biosensor array is first used to determine the anatomical location of the motor point in a test population. This is done by positioning the mapping biosensor array on a test subject's anatomy using a known anatomical landmark, and then using the sensor cells of the detection electrode grid to find the location of the motor point relative to the known anatomical landmark. This then defines the likely anatomical location of the motor point for the general population. From this determination, a diagnostic biosensor array can be configured so that it will perform well for a majority of the general population. More particularly, using the information derived from the mapping biosensor array (i.e., the location of the motor point relative to known anatomical landmark), the diagnostic biosensor array can be configured so that it has its detection electrode reliably positioned over the motor point when the diagnostic sensory array is positioned relative to a selected anatomical landmark. As a result, when the diagnostic biosensor array is disposed on the patient relative to the known anatomical landmark, both the stimulation electrode and the detection electrode will be properly positioned on the patient relative to the pertinent anatomy.

A similar approach can be used to find the optimal detection site for other neuromuscular measurements, and to fabricate an appropriate diagnostic biosensor array for use in the same.

In one preferred embodiment of the present invention, either or both of the mapping biosensor array and/or the diagnostic biosensor array may be enclosed within a housing for temporary attachment to the wrist (or other anatomical structure) of the individual. The housing contains an attachment mechanism (e.g., a non-irritating adhesive material) for securing the housing to the arm (or other anatomical structure) of the individual, and may be disposable. The housing preferably has a connector for electrically connecting the various electrodes, etc. of the mapping biosensor array and/or diagnostic sensor array to an automated test device, e.g., an automated test device of the sort disclosed in U.S. Pat. No. 5,976,094 to Gozani and comprising an electrical stimulator, a signal detector, and a signal processor, as described above.

The housing preferably comprises the stimulation and detection electrodes. If desired, certain components commonly associated with the stimulation electrode (e.g., a temperature sensor, an electronic serial number memory, and/or a reference electrode, etc.) may also be provided.

In one preferred form of the invention, there is provided a mapping biosensor array for locating a point over a muscle or a point over a sensory nerve of a test subject, the mapping biosensor array comprising:
  a body comprising a reference point;
  a stimulation electrode for applying an electrical stimulus to a test subject, the stimulation electrode being mounted to the body in a first fixed relation to the reference point; and
  a detection electrode grid for detecting a bioelectrical signal generated by a test subject in response to the electrical stimulus applied by the stimulation electrode, the detection electrode grid being mounted to the body in a second fixed relation to the reference point;
    wherein the detection electrode grid comprises a plurality of sensor cells, and further wherein each of the sensor cells is configured to independently detect a bioelectrical signal generated by the test subject in response to the electrical stimulus applied by the stimulation electrode.

In another preferred form of the invention, there is provided a diagnostic biosensor array for detecting a bioelectrical signal over a muscle or over a sensory nerve of a patient, the diagnostic biosensor array comprising:
  a body comprising a reference point;
  a stimulation electrode for applying an electrical stimulus to a patient, the stimulation electrode being mounted to the body in a first fixed relation to the reference point; and
  a detection electrode for detecting a bioelectric potential generated by the patient in response to the electrical stimulus applied by the stimulation electrode, the detection electrode being mounted to the body in a second fixed relation to the reference point;
    wherein the second fixed relationship is determined by previously conducting electrophysiological mapping in a plurality of test subjects using a mapping biosensor array.

In another preferred form of the invention, there is provided a method of quickly and non-invasively determining the location of a point over a muscle or a point over a sensory nerve of a test population, the method comprising the steps of:
  providing a mapping biosensor array for locating a point over a muscle or a point over a sensory nerve of a test subject, the mapping biosensor array comprising:
    a body comprising a reference point;
    a stimulation electrode for applying an electrical stimulus to a test subject, the stimulation electrode being mounted to the body in a first fixed relation to the reference point; and
    a detection electrode grid for detecting a bioelectrical signal generated by a test subject in response to the electrical stimulus applied by the stimulation electrode, the detection electrode grid being mounted to the body in a second fixed relation to the reference point;
      wherein the detection electrode grid comprises a plurality of sensor cells, and further wherein each of the sensor cells is configured to independently detect a bioelectrical signal generated by the test subject in response to the electrical stimulus applied by the stimulation electrode;
  positioning the mapping biosensor array on a test subject so that the reference point is positioned relative to a known anatomical landmark;
  applying an electrical stimulus to the test subject;
  measuring an evoked bioelectrical response at each of a plurality of sensor cells; and
  repeating the foregoing process for a plurality of test subjects so as to determine, for the majority of the test subjects, a sensor cell associated with the optimal bioelectrical response.

In another preferred form of the invention, there is provided a method for detecting a bioelectrical signal over a muscle or over a sensory nerve of a patient, the method comprising:
  providing a diagnostic biosensor array comprising:
    a body comprising a reference point;
    a stimulation electrode for applying an electrical stimulus to a patient, the stimulation electrode being mounted to the body in a first fixed relation to the reference point; and
    a detection electrode for detecting a bioelectric potential generated by the patient in response to the electrical stimulus applied by the stimulation electrode, the detection electrode being mounted to the body in a second fixed relation to the reference point;
      whereby the second fixed relationship is determined by previously conducting electrophysiological mapping in a plurality of test subjects;
  positioning the diagnostic biosensor array on a patient so that the reference point is positioned relative to a known anatomical landmark;
  applying an electrical stimulus to the patient; and
  measuring an evoked bioelectrical response in response to the electrical stimulus applied by the stimulation electrode.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE INVENTION

Overview

As is well known to those skilled in the art of analyzing bioelectric signals, it is generally desirable to operate on waveforms which have as large an amplitude as possible. This increases the signal-to-noise ratio and makes key waveform features easier to discern, thereby providing better information that is critical to the quality and effectiveness of manual or automated signal processing. These benefits result in more accurate neurophysiological measurements, e.g., such as for the assessment of neuromuscular function.

In the following discussion, the motor point is used as an illustrative, but not exclusive, example of (i) finding the desired detection site for neuromuscular testing, and (ii) using that detection site to conduct over-muscle and/or over-nerve testing.

The over-muscle signal recorded at the motor point has a significantly greater amplitude than a volume-conducted signal for the same muscle. The myoelectrical signal that results from the stimulation of the nerve that innervates the muscle is known as the Compound Muscle Action Potential (CMAP). This description of the invention will use the motor point of the median nerve of the left hand as an illustrative example of the novel and useful way in which the present invention improves the measurement of neurological signals. However, it should be appreciated that the method and apparatus of the present invention can also be beneficially applied to other upper extremity motor nerves such as the median nerve in the right hand or the ulnar nerve of either side, left or right lower extremity motor nerves such as the peroneal nerve, other motor nerves of the neck and torso, etc.

In addition to assessing motor nerve function, the method and apparatus of the present invention can also be used to assess sensory nerve function. Among other things, the present invention can be beneficially applied to sensory nerves of the upper and lower extremities, as well as sensory nerves of the neck, torso, etc.

Figure 1:
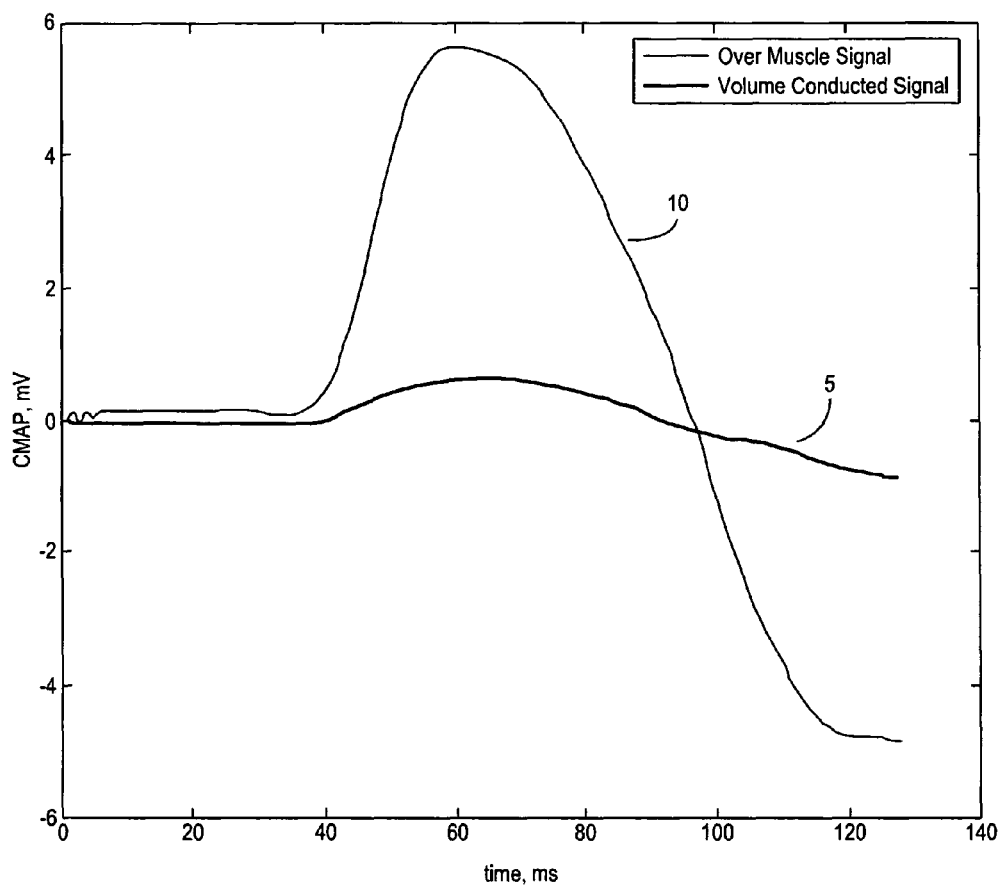
FIG. 1 illustrates the relative amplitudes of (i) a volume-conducted Compound Muscle Action Potential (CMAP), and (ii) an over-muscle Compound Muscle Action Potential (CMAP), for the same subject.

FIG. 1 illustrates the relative amplitudes of a volume-conducted Compound Muscle Action Potential (CMAP) 5 compared with an over-muscle Compound Muscle Action Potential (CMAP) 10, with the myoelectrical potentials being recorded from the same individual. FIG. 1 clearly shows that the amplitude of the over-muscle signal 10 is significantly larger than the amplitude of the volume-conducted signal 5. Table 1, which is an average of 30 CMAP amplitudes recorded from 30 hands of 15 individuals, further illustrates the greater amplitude of the over-muscle signal in a larger test population.

As can be seen in FIG. 1 and in the data of Table 1, the amplitude of the over-muscle CMAP signal 10 is approximately 8 to 10 times larger than the corresponding amplitude of the volume-conducted CMAP signal 5 for the same muscle in the same individuals and is, therefore, a more desirable signal to use for analysis and diagnostic purposes. However, as noted above, the over-muscle recording must be made in such a way that the detection electrodes consistently overlie the motor point. If the spatial relationship (e.g., distance) between the detection electrode and the motor point varies significantly from one individual to another, or if the motor point is entirely missed by the detection electrodes, then the recorded amplitude may be highly variable and, in some cases, the CMAP waveform may have artifacts, all of which may lead to errors in the assessment of the CMAP waveform, e.g., its latency and amplitude. This in turn reduces the accuracy of neuromuscular assessments made using the CMAP waveform.

In the present invention, a mapping biosensor array is used to determine, relative to certain reliable anatomical landmarks, the optimal location for recording motor and sensory responses for the majority of the population. This information can then be used to fabricate a counterpart diagnostic biosensor array which, when placed on an individual using those same reliable anatomical landmarks, automatically positions the detection electrode over the optimal location for recording motor and/or sensory responses on that individual. Stated another way, with the present invention, a mapping biosensor array is first used to identify, relative to reliable anatomical landmarks, the optimal detection site for the majority of the population; and then a diagnostic biosensor array is fabricated using this information so that when the diagnostic biosensor array is positioned on an individual using the reliable anatomical landmarks, the detection electrode is automatically positioned over the optimal detection site.

Determining the Optimal Location for Recording Motor and/or Sensory Responses for the Majority of the Population The mapping biosensor array is used to determine the detection site which will yield an optimal CMAP amplitude for the majority of the population.

In accordance with the present invention, it has been determined that the optimal detection site for recording motor and/or sensory responses generally has the following characteristics:

(i) it yields a large CMAP amplitude within a small percentage (e.g., 10%) of the maximum obtainable amplitude;

(ii) it is over the motor point, so there is minimal risk of initial positivity, which could occur if the detection site is off the motor point but overlying muscle; and (iii) it yields consistent CMAP signals, across multiple applications of the biosensor over time in the same individual, i.e., it provides highly reproducible CMAP measurements.

In accordance with the present invention, and using the mapping biosensor array as will hereinafter be discussed in more detail, the myoelectrical signals are systematically mapped across the abductor pollicis brevis muscle of the hand. This is done using a detection electrode grid which comprises a plurality of sensor cells which overlie the potential optimal detection sites—by detecting the myoelectrical signals at each of the sensor cells and comparing the same, the optimal detection site can be determined.

Other muscles in the body that are innervated by other nerves of medical interest can be similarly mapped.

Likewise, sensory nerves in the body that are of medical interest can be correspondingly mapped.

Figure 2:
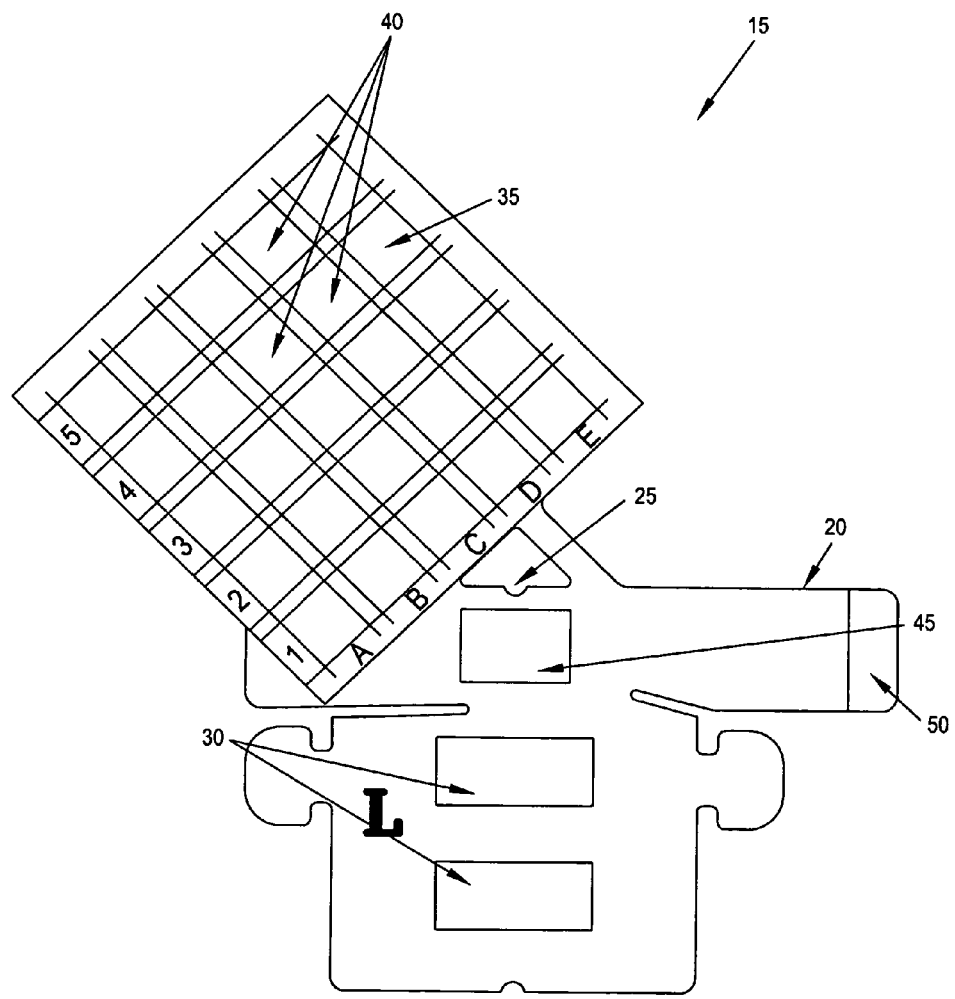
FIG. 2 illustrates a preferred embodiment of a mapping biosensor array formed in accordance with the present invention, showing two stimulation electrodes disposed in a fixed geometric relationship to (i) a detection electrode grid, and (ii) a reference point for positioning relative to a known anatomical landmark.

Looking now at FIG. 2, there is shown a mapping biosensor array 15 formed in accordance with the present invention. Mapping biosensor array 15 generally comprises a body 20 which includes a reference point 25. In one preferred form of the invention, reference point 25 comprises a notch formed in the periphery of body 20. Alternatively, other forms of reference points may be provided, e.g., a through-hole formed in body 20, a printed mark on a clear body, etc. Body 20 also comprises at least one stimulation electrode 30 and a detection electrode grid 35. Detection electrode grid 35 itself comprises a plurality of sensor cells 40, each of which is independently readable. A 5×5 detection electrode grid, or a detection electrode grid with a greater or lesser number of sensor locations, can be used, depending upon the desired resolution of the detection electrode grid.

Body 20 may also comprise a reference electrode 45, or other components well known in the art of detecting bioelectric signals, e.g., a temperature sensor (not shown).

Body 20 also comprises the electrical traces (not shown) for connecting stimulation electrodes 30, detection electrode grid 35, reference electrode 45 (if one is provided), and any other on-board electrical components, with an electrical connector 50. Electrical connector 50 is used to electrically connect mapping biosensor array 15 with an automated test device, e.g., an automated test device generally similar to that disclosed in U.S. Pat. No. 5,976,094 to Gozani and comprising an electrical stimulator, a signal detector, and a signal processor, but modified so as to (i) independently monitor the biopotential signals detected at each of the sensor cells 40, and (ii) determine the cell or cells detecting the highest biopotential signals, as will hereinafter be disclosed.

Stimulator electrodes 30 and detection electrode grid 35 are in a fixed geometric relationship to one another and to reference point 25. As a result, when the reference point 25 is positioned against a reliable anatomical landmark (e.g., the intersection of the longitudinally-extending palmaris longus tendon and the transversely-extending wrist crease 55, shown in FIG. 3), the stimulation electrodes 30 and detection electrode grid 35 will be positioned in a fixed geometric relationship to the reliable anatomical landmark.

Figure 3:
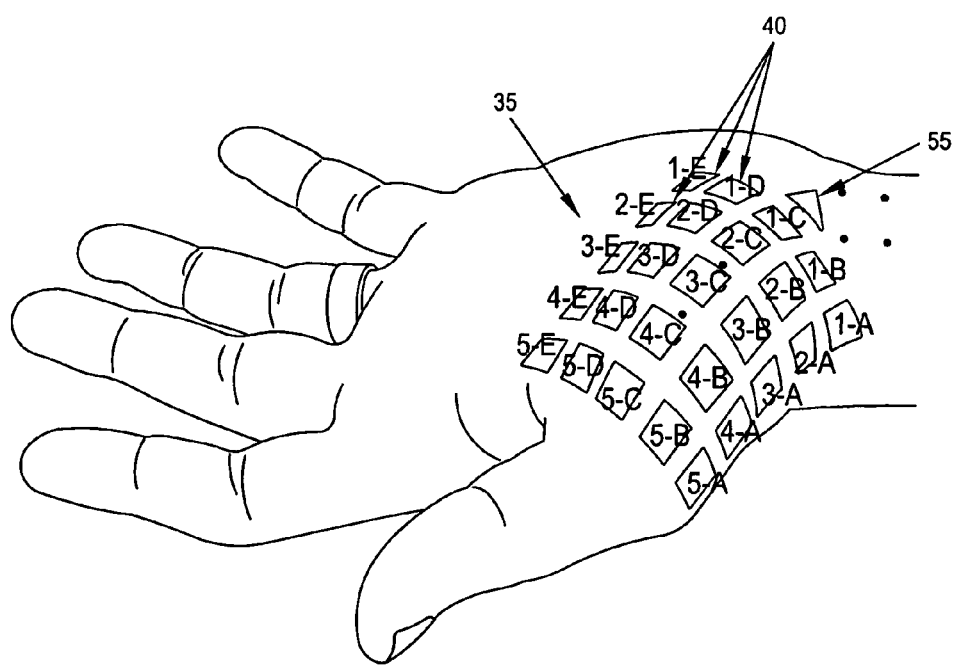
FIG. 3 illustrates the map grid of the mapping biosensor array of FIG. 2 superimposed on the hand of an individual.

FIG. 3 illustrates how the detector electrode grid 35 of FIG. 2 will overlie a typical hand when the mapping biosensor array is positioned on the hand so that the array's reference point 25 is positioned at the known anatomical landmark 55 (which is formed at the intersection of the longitudinally-extending palmaris longus tendon and the wrist crease). Note how each of the sensor cells 40 of detection grid 35 is positioned in a fixed geometric relationship to stimulation electrodes 30 and reference point 25. The distance between the sensor cells 40 is preferably 2.5 mm, each sensor cell 40 is preferably 10 mm square, and the center-to-center distance of the sensor cells is preferably 12.5 mm. A detection electrode grid 35 with a higher or lower distance between sensor cells, bigger or smaller sensor cell size, and/or bigger or smaller center-to-center distances can also be used, depending on the desired resolution of the detection electrode grid 35 and the resulting precision in locating the motor point.

As noted above, mapping biosensor array 15 is used to locate the motor point. This is preferably effected by using the mapping procedure shown in flowchart form in FIGS. 4-6.

Figure 4:
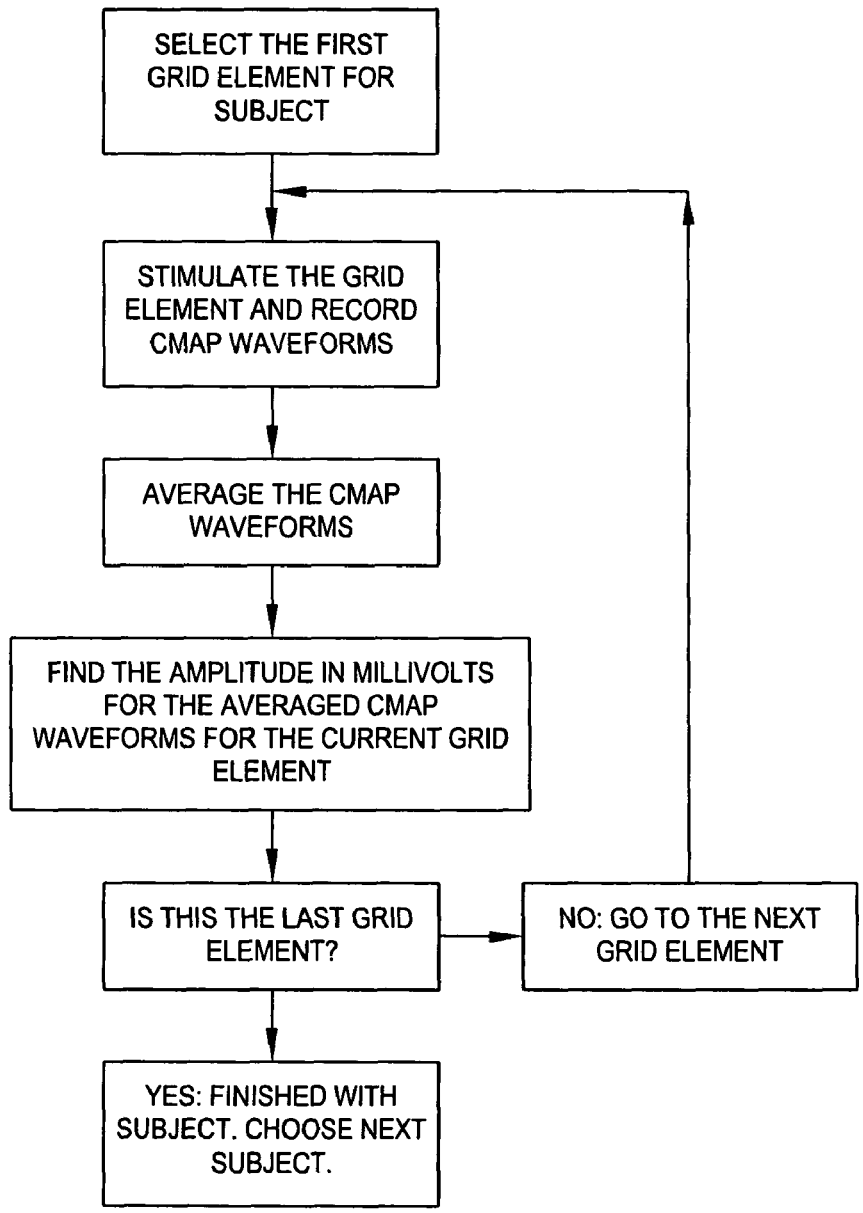
FIG. 4 is a flowchart illustrating one method for determining, for each individual, the CMAP amplitude for each sensor cell of the detection electrode grid.

Looking first at FIG. 4, the mapping procedure is carried out in each of a plurality of test subjects. These test subjects are selected so that they encompass substantially the entire range (e.g., 95%) of anatomical variation that would occur in the individuals in which the diagnostic biosensor array (see below) is intended to be used. For example, hand size is known to vary significantly with height and gender. The variation in hand size, and gender, may affect the location of the motor point vis-à-vis the known anatomical landmark. Therefore, in order to determine the optimal detection site(s), it is important to sample a relatively large test population which is reflective of the general population.

FIG. 4 provides a flowchart of the procedure applied to each of the plurality of test subjects noted above. More particularly, first the mapping biosensor array 15 is applied to the subject, with the reference point 25 overlying the intersection of the palmaris longus tendon and the wrist crease, so that the stimulation electrodes 30 overlie the median nerve and the detection electrode grid 35 overlies the abductor pollicis muscle. Each sensor cell 40 in detection electrode grid 35 is then singly (i.e., individually) selected and, while connected to a neurological recording apparatus, monitored for a myoelectrical signal while an electrical stimulus is applied to the median nerve via a stimulation electrode 30. More particularly, the median nerve is stimulated through one of the stimulator electrodes 30, using a standard neurological test apparatus of the sort designed to evoke a CMAP response. This waveform is detected by a first sensor cell 40 in detection electrode grid 35 and recorded. In some cases, such as when the signal-to-noise ratio is low, it may be advantageous to record the average response to a plurality of identical stimuli at each grid location. The next sensor cell 40 in the detection electrode grid is then connected, a stimulus applied to the nerve, and a reading recorded, and then this process is repeated for each of the grid locations over the abductor pollicis brevis muscle (or other muscle or nerve, depending on the anatomy being tested) until data is collected for all grid locations.

This process is repeated for each test subject until a full grid of signal readings has been collected for each test subject.

The next step in the process is to analyze the data to determine which grid elements are associated with the optimum response signal.

Figure 5:
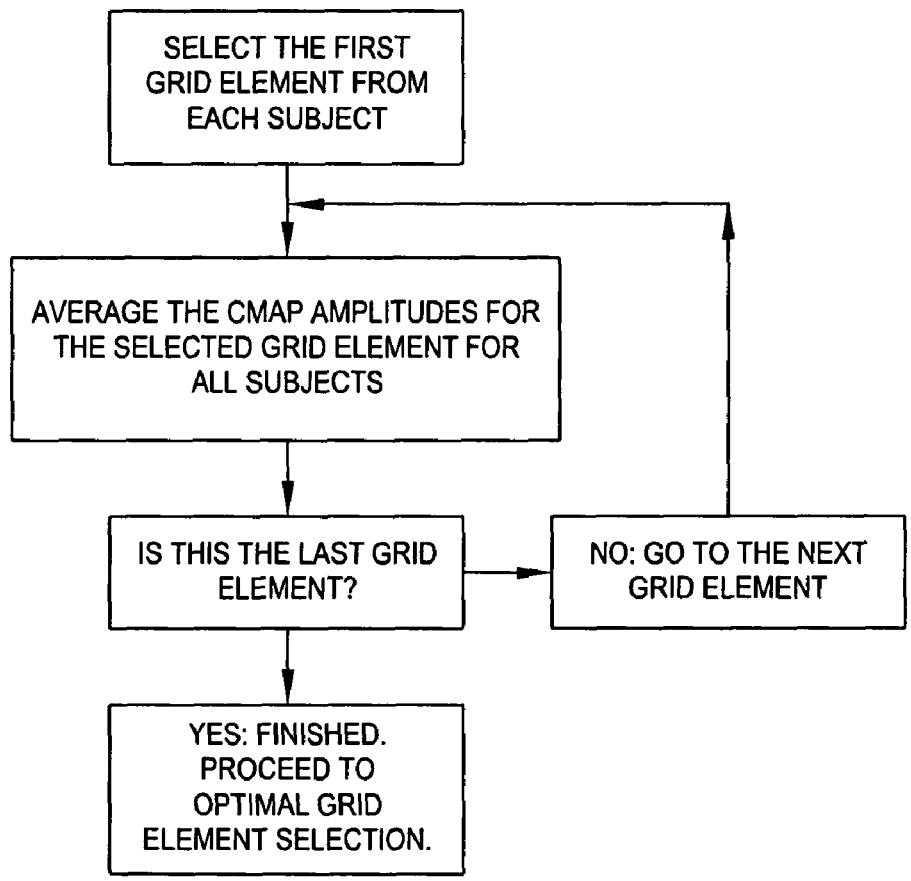
FIG. 5 is a flowchart illustrating one method for mapping the sensor cells of the detection electrode grid across individuals, according to CMAP amplitude.
Figure 7:
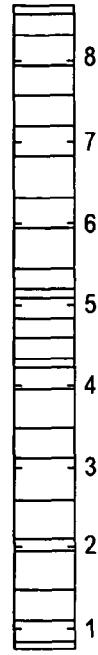
FIG. 7 shows the CMAP amplitudes (in millivolts) of the muscle responses (averaged over ten individuals) that correspond to the sensor cells of the detection electrode grid shown in FIG. 3.

FIG. 5 provides a flowchart of the procedure to map the CMAP amplitude of each grid element so that the CMAP amplitudes of the various grid elements can be compared and the grid elements having the most robust CMAP amplitudes identified. This is important because the locations of the grid elements having the highest CMAP amplitudes are the locations which should be covered by the detection electrode of the corresponding diagnostic biosensor array, as will hereinafter be discussed. In accordance with the flowchart of FIG. 5, the first grid element is selected from each subject and the CMAP amplitude is averaged across all subjects so as to determine the average CMAP amplitude for the first grid element. This process is then repeated until an average CMAP amplitude has been computed for each grid element. A composite grid of averaged CMAP amplitudes can then be assembled, containing the averaged CMAP amplitude value computed across all subjects. An example of the results of that composite CMAP grid (in millivolts of CMAP amplitude) is shown in FIG. 7 for a population of 10 subjects.

Figure 6:
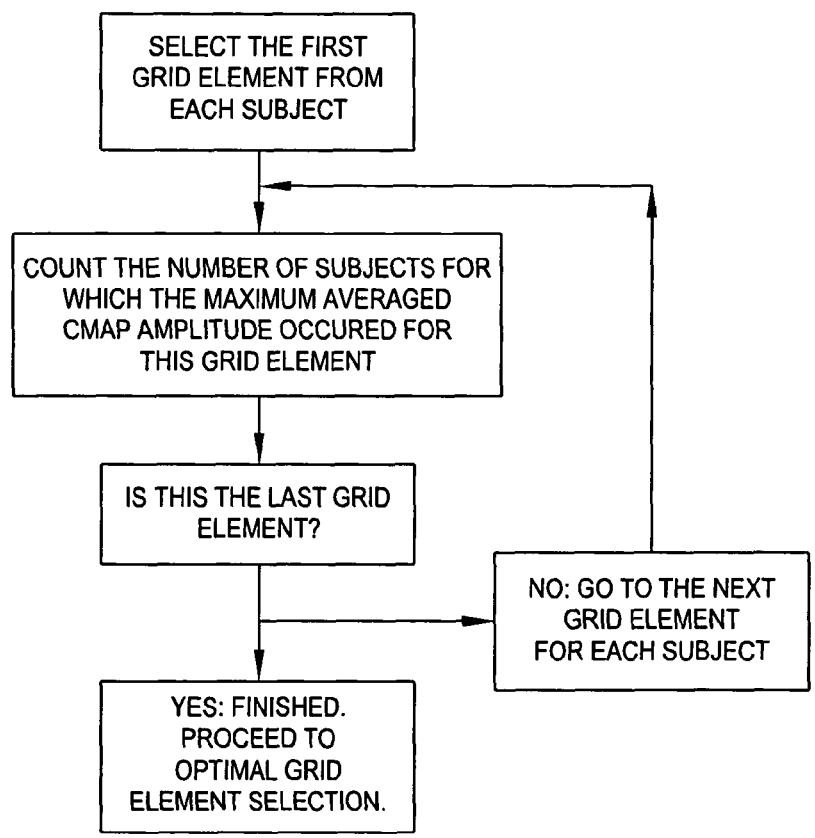
FIG. 6 is a flowchart illustrating another method for mapping the sensor cells of the detection electrode grid across individuals, using the frequency of maximum CMAP amplitude for each sensor cell.

FIG. 6 is a flowchart of an alternative method for determining which grid locations(s) most closely identify the optimal detection site. This alternative method is based on mapping the frequency of the occurrence of the maximum CMAP amplitude for each grid element location across the test group. More particularly, the first grid element is selected. Then the number of subjects for which the maximum averaged CMAP amplitude occurred for this grid element is counted. This process is repeated for each grid element, and then a composite grid is assembled, containing for each grid element the number of times that the grid location had the maximum CMAP value. This alternative method, and other alternate arithmetic methods, can be used to similarly produce a map of grid values that rank the relative importance of each grid element vis-à-vis maximum CMAP amplitude, and hence the relative importance of each grid location in the final detection electrode which is to be located over the motor point.

Figure 8:
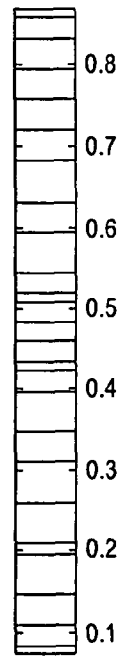
FIG. 8 shows the normalized CMAP amplitudes of the muscle responses (averaged over ten individuals) that correspond to the sensor cells of the detection electrode grid shown in FIG. 3.

The final step in the process is to determine which grid locations should be covered by the optimal detection electrode configuration so as to acquire the optimal CMAP response with the diagnostic biosensor array. For example, one criterion could be to use all contiguous detection sites above a certain percentage of the maximum. Normalizing the millivolt values of FIG. 7 yields the normalized values of FIG. 8, which can help make the relative values across the composite CMAP grid of FIG. 7 more evident. In the illustrative example of FIG. 8, this percentage threshold might be 60%. As can be seen in FIG. 8, the grid locations 2-B, 2-C, 3-B and 3-C all have a CMAP response that meets this criterion. Those locations then collectively represent the area on the hand that lies over the optimal motor point. Thus, a biopotential signal detected at this location yields, for the great majority of the population, the most reliable and discernible information for the most accurate assessment of neuromuscular function.

An alternative approach could be to select the desired grid locations on the basis of the frequency with which they contain the maximum average CMAP amplitude, as described in the flowchart of FIG. 6. This method, and other methods and/or criteria, can be used to include or exclude grid locations, according to the desired neurological testing requirements.

Certain muscles have multiple motor points, e.g., the abductor hallucis muscle in the foot. Therefore, in applying a selection criterion, an alternative method would be to select non-contiguous grid elements to include multiple motor points over one muscle, resulting in multiple optimum motor points. The diagnostic biosensor array can then be constructed so as to have (i) a single detection electrode with multiple islands of sensor cells, or (ii) multiple detection electrodes. In one embodiment of the present invention, when there are multiple islands of grid elements on the detection electrode of the diagnostic biosensor array, all of the elements are connected together so as to simultaneously record the evoked response under all of the grid elements, thereby generating an averaged response representative of all the grid elements. In an alternative embodiment of the present invention, the multiple islands of grid elements are not connected together and, instead, have their outputs fed into distinct recording channels, thereby allowing a diagnostic biosensor array using this invention to record each island of grid elements independently. The need for this alternate method is obvious to one skilled in the art.

Figure 9:
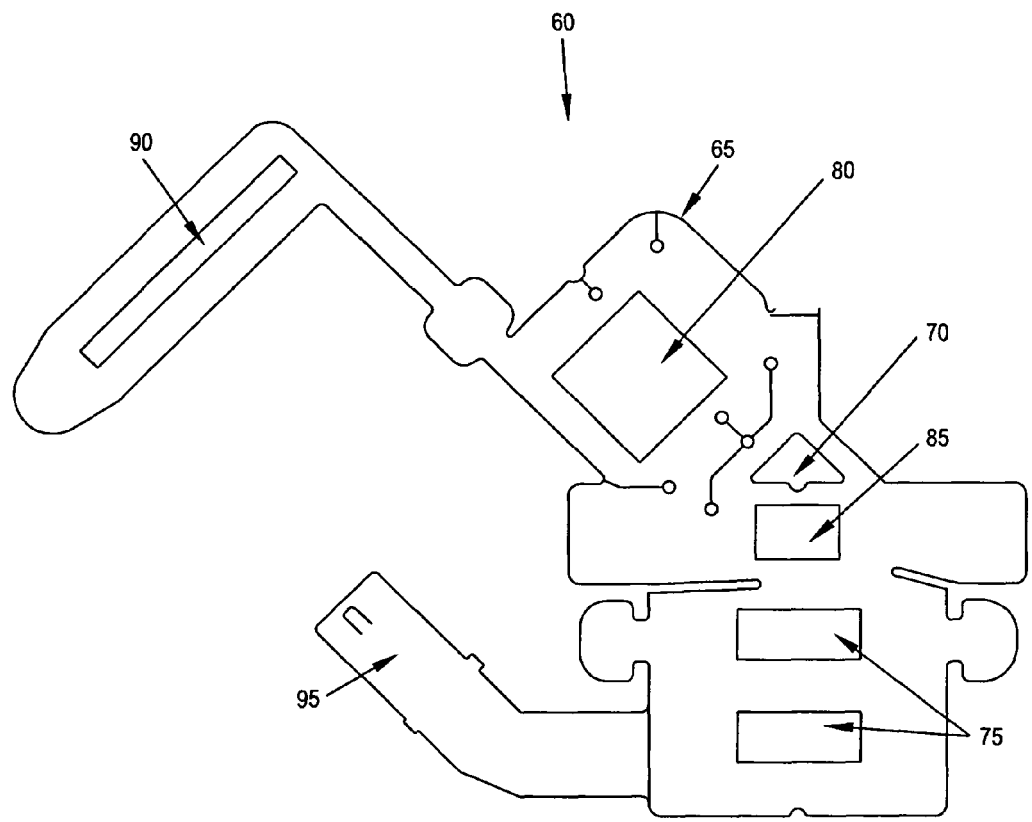
FIG. 9 illustrates one preferred embodiment of a diagnostic biosensor array formed in accordance with the present invention, with the diagnostic biosensor array's detector electrode encompassing the area of those sensor cells of the mapping biosensor array's detection electrode grid that detected the optimal myoelectrical signal (i.e., the sensor cells of the detection electrode grid which were disposed over the motor point); and Table 1 shows over-muscle CMAP amplitude at the motor point vs. volume-conducted CMAP amplitude (in millivolts), averaged over 30 waveforms in the abductor pollicis brevis muscle in the left and right hands of 15 different individuals.

Constructing a Novel Diagnostic Biosensor Array Using the Information Obtained by the Novel Mapping Biosensor Array The information obtained by the mapping biosensor array (i.e., the grid location overlying the motor point) is then used to fabricate a diagnostic biosensor array having a fixed geometry, such that its detection electrode will be reliably positioned over the motor point even when the diagnostic biosensor array is applied to the patient by an individual lacking specialized neurological training. Looking next at FIG. 9, there is shown a diagnostic biosensor array 60 formed in accordance with the present invention. Diagnostic biosensor array 60 generally comprises a body 65 which includes a reference point (preferably a notch, or a through-hole or a printed mark, etc.) 70. Body 65 also comprises at least one stimulator electrode 75 and a detection electrode 80. The grid locations identified by mapping biosensor array 15 as corresponding to the motor point (i.e., locations 2-B, 2-C, 3-B and 3-C in the forgoing example) are spanned by the electrode 80 to cover the optimal motor point when reference point 70 is applied to the known anatomical landmark. Multiple motor points would be constructed in a similar way.

Because of the potentially wide variations in anatomical relationships between reference point 70 and the optimal detection sites, it may be necessary to utilize more than one fixed geometric relationship between reference point 70 and the detection site. For example, there may be two fixed relationships—one for each gender. Alternatively, and as a further example, there may be three fixed relationships for three different height ranges—one for short, medium and tall. The decision as to which fixed configuration to use may then be keyed to these demographic variables. As a result, there may be multiple diagnostic biosensor arrays for a specific nerve measurement.

Body 65 may also comprise a reference electrode 85, or other components well known in the art of detection bioelectric signals, e.g., a temperature sensor (not shown). Body 20 may also comprise an inactive electrode 90.

Body 65 also comprises the electrical traces (not shown) for connecting stimulation electrode 75, detection electrode 80, reference electrode 85 (if one is provided), and any other on-board electrical components, with connection tail 95. Connection tail 95 is used to electrically connect diagnostic biosensor array 60 with an automated test device, e.g., an automated test device generally similar to that disclosed in U.S. Pat. No. 5,976,094 to Gozani and comprising an electrical stimulator, a signal detector, and a signal processor.

Testing Neuromuscular Function Using the Novel Diagnostic Biosensor Array

Diagnostic biosensor array 60 is used to test neuromuscular function. This is done by positioning diagnostic biosensor array 60 on the patient so that reference notch 70 is positioned on the known anatomical landmark. The use of reference notch 70 ensures that detection electrode 80 is positioned directly over the motor point even when deployment is effected by an individual not having specialized neurological training.

Once this has been done, the diagnostic biosensor array has its connection tail connected to an automated test device, and then neuromuscular function is tested in the usual manner.

Alternative Constructions

In the preceding examples, the detection grid elements of mapping biosensor array 15 were chosen based on certain optimal characteristics in a single population of subjects, e.g., those grid elements that provide a CMAP amplitude within a certain fraction of the maximum amplitude.

In another embodiment of the present invention, the grid elements of mapping biosensor array 15 may be chosen based on differentiating two or more populations of subjects. As a specific example, the hands of two populations of subjects could be mapped with the detection electrode grid 35 as described above. One population might be individuals without evidence of neuropathy. The second population might be individuals with clinical or other indicators of neuropathy, such as Carpal Tunnel Syndrome (CTS). The grid elements could then be chosen based on their tendency to separate the two populations. For example, contiguous elements could be chosen that generate CMAPs with maximally different onset latencies. In order to perform this calculation, the average onset latency at each grid element is calculated for each population. A fraction, e.g., 25%, of grid elements with the greatest onset latency difference between the two populations is used and translated into a diagnostic biosensor array 60.

In another embodiment, two populations of subjects with different types of neuropathy, e.g., Carpal Tunnel Syndrome (CTS) and diabetic neuropathy, could be used to determine optimal detector sites.

In yet another embodiment, three or more populations of subjects, e.g., those without neuropathy, those with lumbosacral radiculopathy, and those with diabetic neuropathy, could be used to determine optimal detector sites based on those sites that maximally separate all three populations.

As will be apparent to those skilled in the art, the present invention allows for the creation of disease-optimized neuromuscular sensors. To those skilled in the art, the application of the present invention to various combinations of subject populations and disease states will be apparent.

It should be appreciated that a primary application of the present invention relates to the use of the mapping biosensor array to determine a motor point, and to the subsequent fabrication of a diagnostic biosensor array to detect a myoelectric signal over that motor point. However, it should be appreciated that the present invention may also be used to determine another point over a muscle, i.e., a point which is not necessarily a motor point. By way of example but not limitation, the present invention may be used to determine a point over a muscle which can differentiate between two different diseases, with that point being different from a motor point. In this case, the mapping biosensor array may be used to locate a point over a muscle which differentiates between two diseases (and is not necessarily a motor point), and the diagnostic biosensor array may be subsequently fabricated to detect a myoelectric signal over that point.

In another embodiment of the present invention, the same population of subjects could be mapped at two or more different times, e.g., at one week, one month and one year apart. The grid elements to be used in the diagnostic biosensor array 60 could be chosen as those that have the lowest variation between the two measurement times. In this embodiment, variation could be measured in terms of the CMAP amplitude, CMAP onset latency, or other response parameters known to those skilled in the art.

In the foregoing discussion, the invention is sometimes discussed in the context of detecting CMAP responses and analyzing their attributes, e.g., amplitude, onset latency, etc. However, it should be appreciated that the present invention can also be utilized in the context of detecting Sensory Nerve Action Potential (SNAP) responses and analyzing their attributes, and/or in detecting and analyzing other nerve responses well known to those skilled in the art, e.g., F-waves, A-waves, etc.

Electrode Construction

The housing of the invention (e.g., body 20 of mapping biosensor array 15 and/or body 65 of diagnostic biosensor array 60) can comprise a conductive pattern deposited (e.g., by silk screening, chemical plating, or other conventional means well known to those skilled in the art) on a substrate material. The substrate material can be clear or colored MYLAR®, e.g., in the range of 0.002 inches to 0.007 inches thick, depending on the desired stiffness. Graphical and textual information is preferably printed on the MYLAR® substrate. The temperature sensor component and/or electronic serial number memory component are (to the extent that they are provided) attached to the conductive traces on the MYLAR® substrate with conductive epoxy, a process well known to those skilled in the art. The temperature sensor component is a commonly available electronic component whose electrical value changes with temperature. The electronic serial number memory component is also a readily available programmable electronic component that is well known to those skilled in the art. The conductive pattern also forms the stimulator and detector electrode areas (e.g., stimulation electrode 30 and detection grid 35 in mapping biosensor array 15, and stimulation electrode 75 and detection electrode 80 in diagnostic biosensor array 60) that contact the skin to stimulate and detect the neuromuscular signals. A layer of polyethylene foam, preferably in the range of 0.030 to 0.060 inches thick, with adhesive applied to one or both sides, and with a release liner covering the adhesive, is selectively die-cut or laser-cut to the desired shape, and is selectively kiss-cut to create peel-away areas for when in actual use. The layer of polyethylene foam is then selectively laminated to the MYLAR® substrate.

A conductive gel layer is silk screened or dispensed over the electrode areas. During use, these areas contact and conform to the skin of the subject to acquire the myoelectrical signal. A protective release liner is applied over the gel areas. The serial number and other information (as desired) is programmed into the electronic memory, and the assembly is finalized after being sealed into a pouch.

CONCLUSION

The disclosed invention provides a novel approach to evaluating neuromuscular physiology. A method and apparatus are described for substantially improving measurement of many different parameters of neuromuscular physiology. This is done by using a mapping biosensor array to locate the motor point or a point over a sensory nerve. The foregoing method and apparatus can then be used to fabricate a diagnostic biosensor array with fixed geometry that can permit clinical personnel, without specific neurophysiology training, to readily acquire a signal over the motor point of the nerve or acquire a sensory signal directly over a sensory nerve. The ability to do this provides an improved and more accurate signal, which in turn facilitates an improved and more accurate diagnosis of neuromuscular function. The method and apparatus of the present invention also eliminates the need for time-consuming sampling by a trained neurologist to find the motor point.

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for detecting a bioelectrical signal over a selected muscle or sensory nerve of a patient, the method comprising:
providing a diagnostic biosensor array of fixed geometry comprising:
a body having thereon a physical reference point;
a stimulation electrode for applying an electrical stimulus to a patient, the stimulation electrode being mounted to the body in a first fixed relation to the physical reference point; and
a detection electrode for detecting a bioelectric potential generated by the patient in response to the electrical stimulus applied by the stimulation electrode, the detection electrode being mounted to the body in a second fixed relation to the physical reference point;
wherein the second fixed relation to the physical reference point is determined by previously conducting electrophysiological mapping in a plurality of test subjects using a mapping biosensor array to build the diagnostic biosensor array, the mapping biosensor array having a mapping array body having thereon a stimulation electrode and detection electrodes comprising a matrix of independently readable sensor cells which can be placed on a patient's body, and having thereon a physical reference point in the periphery of the mapping array body from which physical placement of the diagnostic biosensor array physical reference point is optimized for a specific location and a specific response; the mapping array body having independently read the mounted signals detected at each of the sensor cells and having determined the cell(s) which detected the highest biopotential signals;
whereby the diagnostic biosensor array is built as a result of previously using the mapping biosensor array;
positioning the diagnostic biosensor array on a patient so that the diagnostic biosensor array reference point is positioned relative to a known anatomical landmark;
applying an electrical stimulus to the patient; and
measuring an evoked bioelectrical response in response to the electrical stimulus applied by the diagnostic biosensor array stimulation electrode.

2. A method according to claim 1 wherein the bioelectrical signal comprises a compound muscle action potential signal.

3. A method according to claim 1 wherein the bioelectrical signal comprises a sensory nerve action potential signal.

4. A method according to claim 1 wherein the second fixed relation is chosen so as to position the detection electrode over the motor point.

5. A method according to claim 1 wherein the diagnostic biosensor array reference point comprises a notch formed in the diagnostic biosensor array body.

6. A method according to claim 1 wherein the diagnostic biosensor array reference point comprises a through-hole formed in the diagnostic biosensor array body.

7. A method according to claim 1 wherein the diagnostic biosensor array reference point comprises a mark placed on the diagnostic biosensor array body.

8. A method according to claim 1 wherein the diagnostic biosensor array comprises a further stimulation electrode.

9. A method according to claim 1 wherein the diagnostic biosensor array comprises a plurality of further detection electrodes.

10. A method according to claim 1 wherein the diagnostic biosensor array further comprises an electrical harness for (i) applying an electrical stimulus to the stimulation electrode, and (ii) receiving a bioelectric potential detected by the detection electrode.

11. A method according to claim 1 wherein the second fixed relationship is a function of at least one of gender, height and weight.

* * * * *